US010725299B2

(12) United States Patent
Patel et al.

(10) Patent No.: US 10,725,299 B2
(45) Date of Patent: *Jul. 28, 2020

(54) CONTROL OF MEDIATED REALITY WELDING SYSTEM BASED ON LIGHTING CONDITIONS

(71) Applicant: ILLINOIS TOOL WORKS INC., Glenview, IL (US)

(72) Inventors: Nishank Patel, Appleton, WI (US); Praveen Dandu, Appleton, WI (US)

(73) Assignee: Illinois Tool Works Inc., Glenview, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/986,327

(22) Filed: May 22, 2018

(65) Prior Publication Data
US 2019/0121131 A1    Apr. 25, 2019

Related U.S. Application Data

(63) Continuation of application No. 15/497,908, filed on Apr. 26, 2017, now Pat. No. 9,977,242, which is a
(Continued)

(51) Int. Cl.
*A61F 9/06* (2006.01)
*G02B 27/01* (2006.01)
(Continued)

(52) U.S. Cl.
CPC ............ *G02B 27/017* (2013.01); *A61F 9/06* (2013.01); *A61F 9/067* (2013.01); *B23K 9/322* (2013.01);
(Continued)

(58) Field of Classification Search
None
See application file for complete search history.

(56) References Cited

U.S. PATENT DOCUMENTS 3,555,239 A    1/1971  Kerth
3,652,824 A    3/1972  Okada
(Continued)

FOREIGN PATENT DOCUMENTS

CA    2725719 A1    6/2012
CA    2778699       11/2012
(Continued)

OTHER PUBLICATIONS

ASH VR1-DIY Homebrew PC Virtual Reality Head Mounted Display HMD,' alrons1972, https://www.youtube.com/Watch?v=VOQboDZqguU, Mar. 3, 2013, YouTube screenshot submitted in lieu of the video itself.
(Continued)

*Primary Examiner* — Joni Hsu
(74) *Attorney, Agent, or Firm* — McAndrews, Held & Malloy, Ltd.

(57) ABSTRACT

An example head-worn device includes a camera, a display device, weld detection circuitry, and pixel data processing circuitry. The camera generates first pixel data from a field of view of the head-worn device. The display device displays second pixel data to a wearer of the head-worn device based on the first pixel data captured by the camera. The weld detection circuitry determines whether a welding arc is present and generates a control signal indicating a result of the determination. The pixel data processing circuitry processes the first pixel data captured by the camera to generate the second pixel data for display on the display device, where a mode of operation of said pixel data processing circuitry is selected from a plurality of modes based on said control signal.

9 Claims, 9 Drawing Sheets

Related U.S. Application Data continuation-in-part of application No. 14/669,380, filed on Mar. 26, 2015, now Pat. No. 9,666,160.

(51) Int. Cl.

| | |
|---|---|
| *G01R 29/08* | (2006.01) |
| *B23K 9/32* | (2006.01) |
| *G06T 19/00* | (2011.01) |
| *G06T 5/00* | (2006.01) |
| *G09G 5/00* | (2006.01) |
| *G09G 5/10* | (2006.01) |
| *G06F 3/14* | (2006.01) |

(52) U.S. Cl.
CPC ............ *G01R 29/08* (2013.01); *G06T 5/009* (2013.01); *G06T 19/006* (2013.01); *G09G 5/006* (2013.01); *A61F 9/061* (2013.01); *G02B 2027/014* (2013.01); *G02B 2027/0138* (2013.01); *G02F 2201/58* (2013.01); *G06F 3/14* (2013.01); *G06T 2207/10048* (2013.01); *G06T 2207/20208* (2013.01); *G09G 5/003* (2013.01); *G09G 5/10* (2013.01); *G09G 2320/066* (2013.01); *G09G 2320/0626* (2013.01); *G09G 2340/10* (2013.01); *G09G 2360/14* (2013.01); *G09G 2360/141* (2013.01); *G09G 2360/144* (2013.01); *G09G 2370/20* (2013.01)

(56) References Cited

U.S. PATENT DOCUMENTS

| | | | |
|---|---|---|---|
| 4,021,840 A | 5/1977 | Ellsworth | |
| 4,280,137 A | 7/1981 | Ashida | |
| 4,477,712 A | 10/1984 | Lillquist | |
| 4,577,796 A | 3/1986 | Powers | |
| 4,641,292 A | 2/1987 | Tunnell | |
| 4,707,647 A | 11/1987 | Coldren | |
| 4,733,051 A | 3/1988 | Nadeau | |
| 4,812,614 A | 3/1989 | Wang | |
| 5,275,327 A | 1/1994 | Watkins | |
| 5,380,978 A | 1/1995 | Pryor | |
| 5,572,102 A | 11/1996 | Goodfellow | |
| 5,580,475 A | 12/1996 | Sakai | |
| 5,923,555 A | 7/1999 | Bailey | |
| 5,932,123 A | 8/1999 | Marhofer | |
| 5,978,090 A | 11/1999 | Burri | |
| 6,122,042 A | 9/2000 | Wunderman et al. | |
| 6,240,253 B1 | 5/2001 | Yamaguchi | |
| 6,242,711 B1 | 6/2001 | Cooper | |
| 6,572,379 B1 | 6/2003 | Sears | |
| 6,587,186 B2 | 7/2003 | Bamji | |
| 6,734,393 B1 | 5/2004 | Friedl | |
| 7,534,005 B1 | 5/2009 | Buckman | |
| 7,926,118 B2 | 4/2011 | Becker | |
| 7,962,967 B2 | 6/2011 | Becker | |
| 7,987,492 B2 | 7/2011 | Liwerant | |
| 8,224,029 B2 | 7/2012 | Saptharishi | |
| 8,274,013 B2 | 9/2012 | Wallace | |
| 8,275,201 B2 | 9/2012 | Rangwala | |
| 8,316,462 B2 | 11/2012 | Becker et al. | |
| 8,502,866 B2 | 8/2013 | Becker | |
| 8,569,655 B2 | 10/2013 | Cole | |
| 8,605,008 B1 | 12/2013 | Prest | |
| 8,680,434 B2 | 3/2014 | Stoger et al. | |
| 8,808,164 B2 | 8/2014 | Hoffman | |
| 8,826,357 B2 | 9/2014 | Fink | |
| 8,915,740 B2 | 12/2014 | Zboray | |
| 8,934,029 B2 | 1/2015 | Nayar | |
| 8,957,835 B2 | 2/2015 | Hoellwarth | |
| 8,964,298 B2 | 2/2015 | Haddick | |
| RE45,398 E | 3/2015 | Wallace | |
| 8,992,226 B1 | 3/2015 | Leach | |
| 9,056,365 B2 | 6/2015 | Hoertenhuber | |
| 9,073,138 B2 | 7/2015 | Wills | |
| 9,097,891 B2 | 8/2015 | Border | |
| 9,101,994 B2 | 8/2015 | Albrecht | |
| 9,235,051 B2 | 1/2016 | Salter | |
| 9,244,539 B2 | 1/2016 | Venable | |
| 9,352,411 B2 | 5/2016 | Batzler | |
| 2002/0017752 A1 | 2/2002 | Levi | |
| 2004/0034608 A1 | 2/2004 | de Miranda et al. | |
| 2004/0189675 A1 | 9/2004 | Pretlove | |
| 2005/0001155 A1* | 1/2005 | Fergason | A61F 9/067 250/221 |
| 2005/0099102 A1 | 5/2005 | Villarreal | |
| 2005/0103767 A1 | 5/2005 | Kainec | |
| 2005/0161357 A1 | 7/2005 | Allan | |
| 2005/0199605 A1 | 9/2005 | Furman | |
| 2006/0087502 A1* | 4/2006 | Karidis | G06F 1/3203 345/211 |
| 2006/0176467 A1 | 8/2006 | Rafii | |
| 2006/0207980 A1 | 9/2006 | Jacovetty | |
| 2006/0213892 A1 | 9/2006 | Ott | |
| 2006/0281971 A1 | 12/2006 | Sauer | |
| 2007/0187378 A1 | 8/2007 | Karakas | |
| 2008/0083351 A1 | 4/2008 | Lippert | |
| 2008/0158502 A1 | 7/2008 | Becker | |
| 2008/0187235 A1 | 8/2008 | Wakazono | |
| 2008/0314887 A1 | 12/2008 | Stoger | |
| 2009/0014500 A1 | 1/2009 | Cho et al. | |
| 2009/0134203 A1 | 5/2009 | Domec et al. | |
| 2009/0231423 A1 | 9/2009 | Becker | |
| 2009/0276930 A1 | 11/2009 | Becker | |
| 2009/0298024 A1 | 12/2009 | Batzler | |
| 2010/0036624 A1* | 2/2010 | Martin | G01R 22/10 702/61 |
| 2010/0206851 A1 | 8/2010 | Nakatate | |
| 2010/0223706 A1 | 9/2010 | Becker | |
| 2010/0262468 A1 | 10/2010 | Blankenship | |
| 2011/0091846 A1 | 4/2011 | Kreindl | |
| 2011/0108536 A1* | 5/2011 | Inada | B23K 9/0953 219/130.1 |
| 2011/0117527 A1 | 5/2011 | Conrardy | |
| 2011/0187859 A1 | 8/2011 | Edelson | |
| 2011/0220616 A1 | 9/2011 | Mehn | |
| 2011/0220619 A1 | 9/2011 | Mehn | |
| 2011/0227934 A1 | 9/2011 | Sharp | |
| 2011/0309236 A1 | 12/2011 | Tian | |
| 2012/0012561 A1 | 1/2012 | Wiryadinata | |
| 2012/0074114 A1 | 3/2012 | Kawamoto | |
| 2012/0152923 A1 | 6/2012 | Sickels | |
| 2012/0176659 A1* | 7/2012 | Hsieh | A61F 9/067 359/272 |
| 2012/0180180 A1 | 7/2012 | Steve | |
| 2012/0189993 A1 | 7/2012 | Kindig | |
| 2012/0229632 A1 | 9/2012 | Hoertenhuber | |
| 2012/0241429 A1* | 9/2012 | Knoener | B23K 9/095 219/130.01 |
| 2012/0249400 A1 | 10/2012 | Demonchy | |
| 2012/0262601 A1 | 10/2012 | Choi | |
| 2012/0291172 A1 | 11/2012 | Wills | |
| 2012/0298640 A1 | 11/2012 | Conrardy | |
| 2012/2298640 | 11/2012 | Conrardy | |
| 2013/0050432 A1 | 2/2013 | Perez | |
| 2013/0081293 A1 | 4/2013 | Delin | |
| 2013/0112678 A1 | 5/2013 | Park | |
| 2013/0189657 A1 | 7/2013 | Wallace | |
| 2013/0189658 A1 | 7/2013 | Peters | |
| 2013/0206740 A1 | 8/2013 | Pfeifer | |
| 2013/0206741 A1 | 8/2013 | Pfeifer | |
| 2013/0208569 A1 | 8/2013 | Pfeifer | |
| 2013/0215281 A1 | 8/2013 | Hobby | |
| 2013/0229485 A1 | 9/2013 | Rusanovskyy | |
| 2013/0234935 A1* | 9/2013 | Griffith | G02B 26/004 345/156 |
| 2013/0291271 A1 | 11/2013 | Becker | |
| 2013/0321462 A1 | 12/2013 | Salter | |
| 2013/0345868 A1 | 12/2013 | One | |
| 2014/0014637 A1 | 1/2014 | Hunt | |
| 2014/0014638 A1 | 1/2014 | Artelsmair | |

(56) References Cited

U.S. PATENT DOCUMENTS

| | | | |
|---|---|---|---|
| 2014/0020147 A1* | 1/2014 | Anderson | A61F 9/06 2/8.2 |
| 2014/0059730 A1 | 3/2014 | Kim | |
| 2014/0063055 A1 | 3/2014 | Osterhout | |
| 2014/0092015 A1* | 4/2014 | Xing | G06K 9/00281 345/158 |
| 2014/0097164 A1 | 4/2014 | Beistle | |
| 2014/0134579 A1 | 5/2014 | Becker | |
| 2014/0134580 A1 | 5/2014 | Becker | |
| 2014/0144896 A1 | 5/2014 | Einav | |
| 2014/0159995 A1 | 6/2014 | Adams | |
| 2014/0183176 A1 | 7/2014 | Hutchison | |
| 2014/0184496 A1 | 7/2014 | Gribetz | |
| 2014/0185282 A1 | 7/2014 | Hsu | |
| 2014/0205976 A1 | 7/2014 | Peters | |
| 2014/0232825 A1 | 8/2014 | Gotschlich | |
| 2014/0263224 A1 | 9/2014 | Becker | |
| 2014/0263249 A1 | 9/2014 | Miller | |
| 2014/0272835 A1 | 9/2014 | Becker | |
| 2014/0272836 A1 | 9/2014 | Becker | |
| 2014/0272837 A1 | 9/2014 | Becker | |
| 2014/0272838 A1 | 9/2014 | Becker | |
| 2014/0320529 A1 | 10/2014 | Roberts | |
| 2014/0326705 A1 | 11/2014 | Kodama | |
| 2015/0009316 A1 | 1/2015 | Baldwin | |
| 2015/0056584 A1 | 2/2015 | Boulware | |
| 2015/0072323 A1 | 3/2015 | Postlethwaite | |
| 2015/0125836 A1 | 5/2015 | Daniel | |
| 2015/0154884 A1 | 6/2015 | Salsich | |
| 2015/0190875 A1 | 7/2015 | Becker | |
| 2015/0190876 A1 | 7/2015 | Becker | |
| 2015/0190887 A1 | 7/2015 | Becker | |
| 2015/0190888 A1 | 7/2015 | Becker | |
| 2015/0194072 A1 | 7/2015 | Becker | |
| 2015/0194073 A1 | 7/2015 | Becker | |
| 2015/0209887 A1 | 7/2015 | DeLisio | |
| 2015/0248845 A1 | 9/2015 | Postlethwaite | |
| 2015/0304538 A1 | 10/2015 | Huang | |
| 2015/0325153 A1 | 11/2015 | Albrecht | |
| 2015/0352653 A1 | 12/2015 | Albrecht | |
| 2015/0375324 A1 | 12/2015 | Becker | |
| 2015/0375327 A1 | 12/2015 | Becker | |
| 2015/0379894 A1 | 12/2015 | Becker | |
| 2016/0027215 A1 | 1/2016 | Burns | |
| 2016/0049085 A1 | 2/2016 | Beeson | |
| 2016/0158884 A1 | 6/2016 | Hagenlocher | |
| 2016/0183677 A1 | 6/2016 | Achillopoulos | |
| 2016/0284311 A1 | 9/2016 | Patel | |
| 2016/0365004 A1 | 12/2016 | Matthews | |
| 2017/0053557 A1 | 2/2017 | Daniel | |
| 2017/0249858 A1 | 8/2017 | Boettcher | |

FOREIGN PATENT DOCUMENTS

| | | |
|---|---|---|
| CN | 1749940 | 3/2006 |
| CN | 101067905 A | 11/2007 |
| CN | 101248659 | 8/2008 |
| CN | 101965576 | 2/2011 |
| CN | 103170767 | 6/2013 |
| CN | 103687687 A | 3/2014 |
| CN | 204013703 | 12/2014 |
| CN | 104384765 | 3/2015 |
| CN | 104599314 | 5/2015 |
| DE | 4313508 A1 | 10/1994 |
| EP | 0165501 | 12/1985 |
| EP | 2082656 A1 | 7/2009 |
| JP | S52126656 | 10/1977 |
| JP | 2002178148 | 6/2002 |
| JP | 2016203205 | 12/2016 |
| WO | 2008101379 A1 | 8/2008 |
| WO | 2009137379 A1 | 11/2009 |
| WO | 2013122805 A1 | 8/2013 |
| WO | 2014188244 | 11/2014 |
| WO | 2015121742 | 8/2015 |
| WO | 2016044680 | 3/2016 |

OTHER PUBLICATIONS

High Dynamic Range (HDR) Video Image Processing for Digital Glass, Augmented Reality in Quantigraphic Lightspace and Mediated Reality with Remote Expert, Raymond Lo, Sep. 12, 2012, https://www.youtube.com/Watch?v=ygcm0AQXX9k, YouTube screenshot submitted in lieu of the video itself.

Optical Head-Mounted Display, Wikipedia, Jun. 2, 2016, https://en.wikipedia.org/wiki/Optical_head-mounted_display 14 pages.

Soldamatic Augmented Training, Augmented Reality World, May 30, 2013, https://www.youtube.com/watch?V=Mn0O52Ow_qY, YouTube screenshot submitted in lieu of the video itself.

"High Dynamic Range (HDR) Video Image Processing for Digital Glass, Wearable Cybernetic Eye Tap Helmet Prototype," Raymond Lo, https://www.youtube.com/watch?v=gtTdiqDqHc8, Sep. 12, 2012, YouTube screenshot Submitted in lieu of the video itself.

About Us.' Weldobot.com. <http://weldobot.com/?page_id=6> Accessed Jun. 2, 2016. 1 page.

AD-081CL Digital 2CCD Progressive Scan HDR/High Frame Rate Camera User's Manual, Jul. 1, 2012 (Jul. 1, 2012) p. 27, XP055269758, Retrieved from the Internet: URL:http://www.stemmer-imaging.de/media/up loads/docmanager/53730_JAI_AD-081_CL_Manual.pdf [retrieved on Apr. 29, 2016] the whole document (55 pages).

Aiteanu, Dorin, "Virtual and Augmented Reality Supervisor for a New Welding Helmet" Nov. 15, 2005, pp. 1-150.

Altasens—Wide Dynamic Range (WDR), http://www.altasens.com/index.php/technology/wdr (1 page).

Aiteanu et al., Generation and Rendering of a Virtual Welding Seam in an Augmented Reality Training Envionment, Proceedings of the Sixth IASTED International Conference Visualization, Imaging, and Image Proceeding, Aug. 28-30, 2006, Palma de Mallorca, Spain ISBN Hardcapy: 0-88986-598-1 /CD: 0-88986-600-7 (8 pages).

Anonymous: "JAI introduces unique high-dynamic-range camera", Nov. 5, 2009 (Nov. 5, 2009), XP055269759, Retrieved from the Internet: URL:http://www.jai.com/en/newsevents/news/ad-081c1 [retrieved on Apr. 29, 2016] Typical HDR applications for the AD-081CL include inspection tasks where incident light or bright reflections are Oresent, such as . . . welding (2 pages).

Bombardier et al: "Dual Digimig/Pulse Feeder and SVI-450i Power Supply", Feb. 1999 (Feb. 1999), XP055480578, Retrieved from the Internet: URL:http://www.esabna.com/eu/literature/arc%20equipment/accessories/dual%20digimig_pulse_fdr%20&%20svi-450i_15-565.pdf [retrieved on Jun. 1, 2018].

Cameron Series: "Why Weld Cameras Need Why High Dynamic Range Imaging", Apr. 10, 2013 (Apr. 10, 2013), XP055269605, Retrieved from the Internet: URL:http://blog.xiris.com/blog/bid/258666/Why-Weld-Cameras-Need-High-Dynamic-Range-Imaging [retrieved on Apr. 29, 2016] the whole document (5 pages).

Cavilux HF, Laser Light for High-Speed Imaging, See What You Have Missed (2 pages).

Cavilux Smart, Laser Light for Monitoring and High Speed Imaging, Welcome to the Invisible World (2 pages).

Choi et al., Simulation of Dynamic Behavior in a GMAW System, Welding Research Supplement, 239-s thru 245-s (7 pages), 2001.

Communication from European Patent Office Appln No. 18 150 120.6 dated Jul. 4, 2018 (9 pgs).

Daqri Smart Helmet, The World's First Wearable Human Machine Interface, Brochure (9 pages).

Electronic speckle pattern interferometry Wikipedia, the free encyclopedia (4 pages) Oct. 9, 2008.

Frank Shaopeng Cheng (2008). Calibration of Robot Reference Frames for Enhanced Robot Positioning Accuracy, Robot Manipulators, Marco Ceccarelli (Ed.), ISBN: 978-953-7619-06-0, InTech, Available from: http://www.intechopen.com/books/robot_manipulators/calibration_of robot_reference_frames_for_enhanced_r obot_positioning_accuracy (19 pages).

(56) References Cited

OTHER PUBLICATIONS

G. Melton et al: "Laser diode based vision system for viewing arc welding (May 2009)", EUROJOIN 7, May 21, 2009 (May 21, 2009), XP055293872, Venice Lido, Italy, May 21-22, 2009.
Handheld Welding Torch with Position Detection technology description, Sep. 21, 2011 (11 pages).
HDR Camera for Industrial and Commercial Use, Invisual E Inc., http://www.invisuale.com/hardware/hdr-camera.html (2 pages), Nov. 16, 2011.
Heston, Tim, Lights, camera, lean-recording manufacturing efficiency, The Fabricator, Aug. 2010 (4 pages).
Hillers, Bernd & Aiteanu, D & Tschirner, P & Park, M & Graeser, Axel & Balazs, B & Schmidt, L. (2004). TEREBES: Welding helmet with AR capabilities.
Hillers, Bernd, lat Institut fur Automatislerungstechnik, doctoral thesis Selective Darkening Filer and Welding Arc Observation for the Manual Welding Process, Mar. 15, 2012, 152 pgs.
Int' Search Report and the Written Opinion Appln No. PCT/US2016/016107, dated May 17, 2016 (11 pages).
Int'l Search Report and Written Opinion for PCT/US2015/067931 dated Jul. 26, 2016 (19 pages).
Int'l Search Report and Written Opinion for PCT/US2016/035473 dated Aug. 17, 2016 (15 pages).
Int'l Search Report and Written Opinion for PCT/US2018/028261 dated Aug. 6, 2018 (17 pgs).
Intelligent Robotic Arc Sensing, Lincoln Electric, Oct. 20, 2014, http://www.lincolnelectric.com/en-us/support/process-and-theory/pages/intelligent-robotic-detail.aspx (3 pages).
Intelligenter SchweiBbrenner, Intelligent Welding Torch, IP Bewertungs AG (IPB) (12 pages).
International Search Report and Written Opinion corresponding to International Patent Application No. PCT/US2016/012164, dated May 12, 2016.
International Search Report and Written Opinion corresponding to International Patent Application No. PCT/US2016/020861, dated May 23, 2016.
Larkin et al., "3D Mapping using a ToF Camera for Self Programming an Industrial Robot", Jul. 2013, IEEE, 2013 IEEE/ASME International Conference on Advanced Intelligent Mechatronics (AIM), pp. 494,499.
Li, Larry, Time-of-Flight Camera—An Introduction, Technical White Paper, SLOA190B—Jan. 2014, revised May 2014 (10 pages).
LiveArc Welding Performance Management System, A reality-based recruiting, screening and training solution, MillerWelds.com 2014 (4 pages).
Lutwak, Dr. Robert, Darpa, Microsystems Tech. Office, Micro-Technology for Positioning, Navigation, and Timing Towards PNT Everywhere and Always, Feb. 2014 (4 pages).
Lutwak, Dr. Robert, Micro-Technology for Positioning, Navigation, and Timing Towards PNT Everywhere and Always Stanford PNT Symposium, Stanford, CA Oct. 29, 2014 (26 pages).
Mnich, Chris, et al., "In situ weld pool measurement using sterovision," Japan-UA Symposium on Flexible Automation, Denver, CO 2004, Jul. 2004.
Ni, Y. et al. A 768×576 Logarithmic Image Sensor with Photodiode in Solar Cell Mode, New Imaging Technologies (4 pges), Oct. 11, 2014.
Ni, Yang, et al., A CMOS Log Image Sensor with On-Chip FPN Compensation (4 pages), Oct. 2001.
NIT Color Management, R&D Report N RD1113-Rev B, Apr. 11, 2011 (31 pages).
NIT Image Processing Pipeline for Lattice HDR-6-, NIP, Pipeline, IP_NIT_NSC1005C_HDR60_V1_0 (23 pages).
NIT Image Processing Pipeline, R&D Report N RD1220-Rev B, May 14, 2012 (10 pages).
NIT, 8Care12004-02-B1 Datasheet, New Imaging Technologies (9 pages).
NIT, Application Note: Native WDRTM for your Industrial Welding Applications, www.new-imaging-technologies.com (2 pages).
NIT, Magic Technology—White Paper, Scene Contrast Indexed Image Sensing with WDR (14 pages).
NIT, NSC1005, Datasheet, Revised Nov. 2012, NSC1005 HD ready Logarithmic CMOS Sensor (28 pages).
NIT, WiDySwire, New Imaging Technologyies (7 pages).
NIT Image Processing Pipeline for Lattice HDR-60, NIP IP Pipeline, NIT_HDR60_V1_0_Pipeline_Sample (48 pages).
OV10642:1.3-Megapixel OmniHDRTM, http://www.ovt.com/applications/application.php?id=7 (2 pages).
Parnian, Neda et al., Integration of a Multi-Camera Vision System and Strapdown Inertial Naviation System (SDINS) with a Modified Kalman Filter, Sensors 2010, 10, 5378-5394; doi: 10.3390/s100605378 (17 pages), Jun. 2010.
Patent Cooperation Treaty, Notification of Transmittal of the International Search Report and the Written Opinion of the International Searching Authority, in PCT/US2016/020865, dated May 11, 2016, 12 pages.
Pipe-Bug, Motorized & Manual Chain Driven Pipe Cutting Machines From Bug-0 Systems (4 pages).
Reverchon, J.L., et al. New InGaAs SWIR Imaging Solutions from III-VLab, New Imaging Technologies (10 pages).
Rivers, et al., Position-Correcting Tools for 2D Digital Fabrication (7 pages), Jul. 1, 2012.
Sergi Foix et al: "Exploitation of Time-of-Flight (ToF) Cameras IRI Technical Report", Oct. 1, 2007 (Oct. 1, 2007), pp. 1-22, XP055294087, Retrieved from the Internet: URL:http://digital.csic.es/bitstream/10261/30066/1 Itime-of-flight.pdf [retrieved on Aug. 8, 2016].
Telops, Innovative Infrared Imaging, HDR-IR High Dynamic Range IR Camera, http://www.telops.com/en/infrared-Cameras/hdr-ir-high-dynamic-range-ir-camera, 2015 (2 pages).
Wavelength Selective Switching, http://en.wikipedia.org/wiki/wavelength_selective_switching, Mar. 4, 2015 (5 pages).
Windows 10 to Get 'Holographic' Headset and Cortana, BBC News, www.bbc.com/news/technology-30924022, Feb. 26, 2015 (4 pages).
European Office Action Appln No. 16713176.2 dated Oct. 17, 2018 (7 pgs).

* cited by examiner

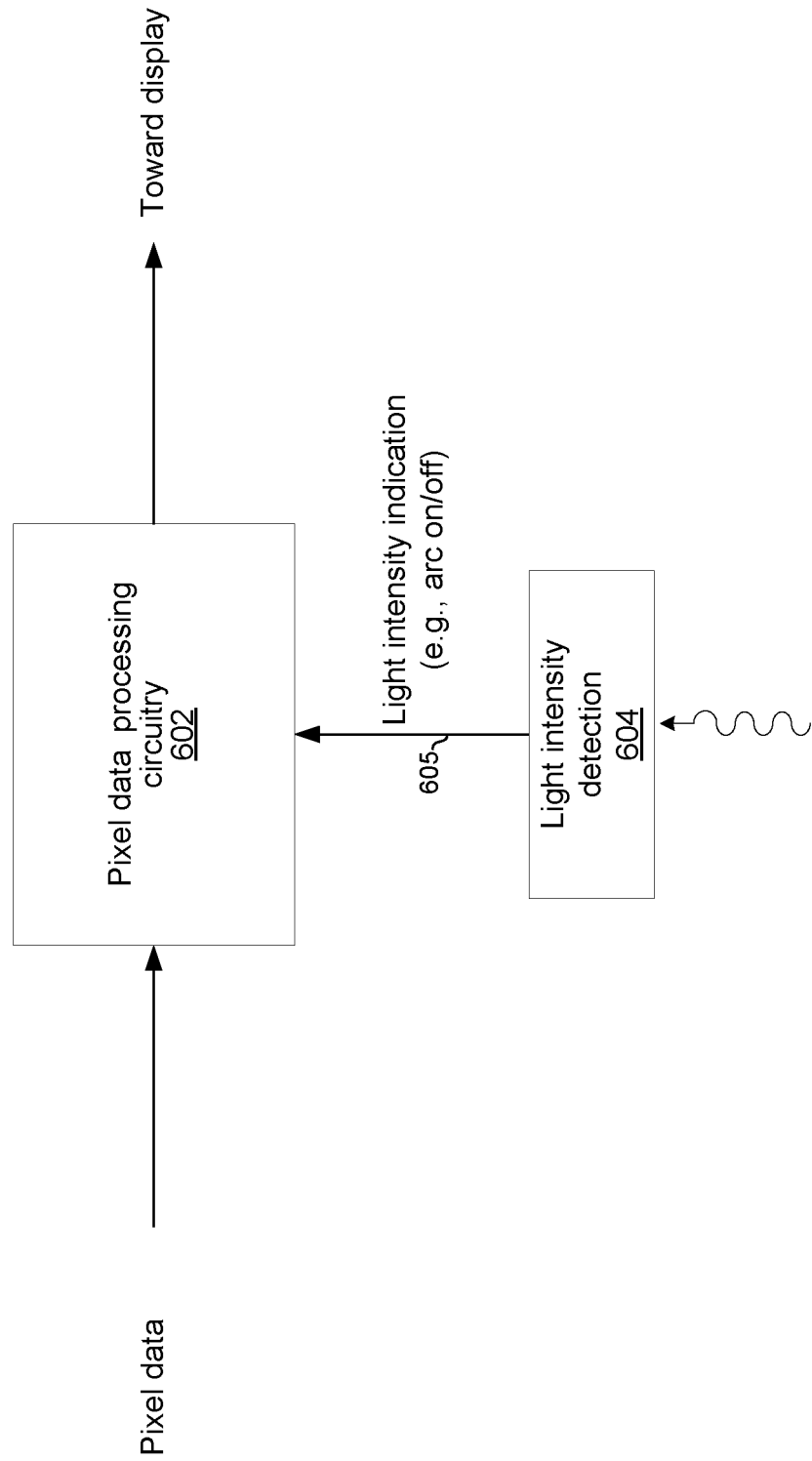

CONTROL OF MEDIATED REALITY WELDING SYSTEM BASED ON LIGHTING CONDITIONS

RELATED APPLICATIONS

This patent application is a continuation of U.S. patent application Ser. No. 15/497,908, filed Apr. 26, 2017, now U.S. Pat. No. 9,977,242, and entitled "Control of Mediated Reality Welding System Based on Lighting Conditions," which is a continuation-in-part of U.S. patent application Ser. No. 14/669,380, filed Mar. 26, 2015, now U.S. Pat. No. 9,666,160, and entitled "Control of Mediated Reality Welding System Based on Lighting Conditions." The entireties of U.S. patent application Ser. No. 14/669,380 and U.S. patent application Ser. No. 15/497,908 are incorporated herein by reference.

BACKGROUND

Welding is a process that has increasingly become ubiquitous in all industries. While such processes may be automated in certain contexts, a large number of applications continue to exist for manual welding operations, the success of which relies heavily on the ability of the operator to see his/her work while protecting his/her eyesight.

BRIEF SUMMARY

Methods and systems are provided for control of mediated reality welding system based on lighting conditions, substantially as illustrated by and/or described in connection with at least one of the figures, as set forth more completely in the claims.

BRIEF DESCRIPTION OF THE DRAWINGS

FIGS. 6A and 6B are block diagrams of example circuitry for controlling pixel data processing based on a detection of light intensity.

DETAILED DESCRIPTION

Figure 1:
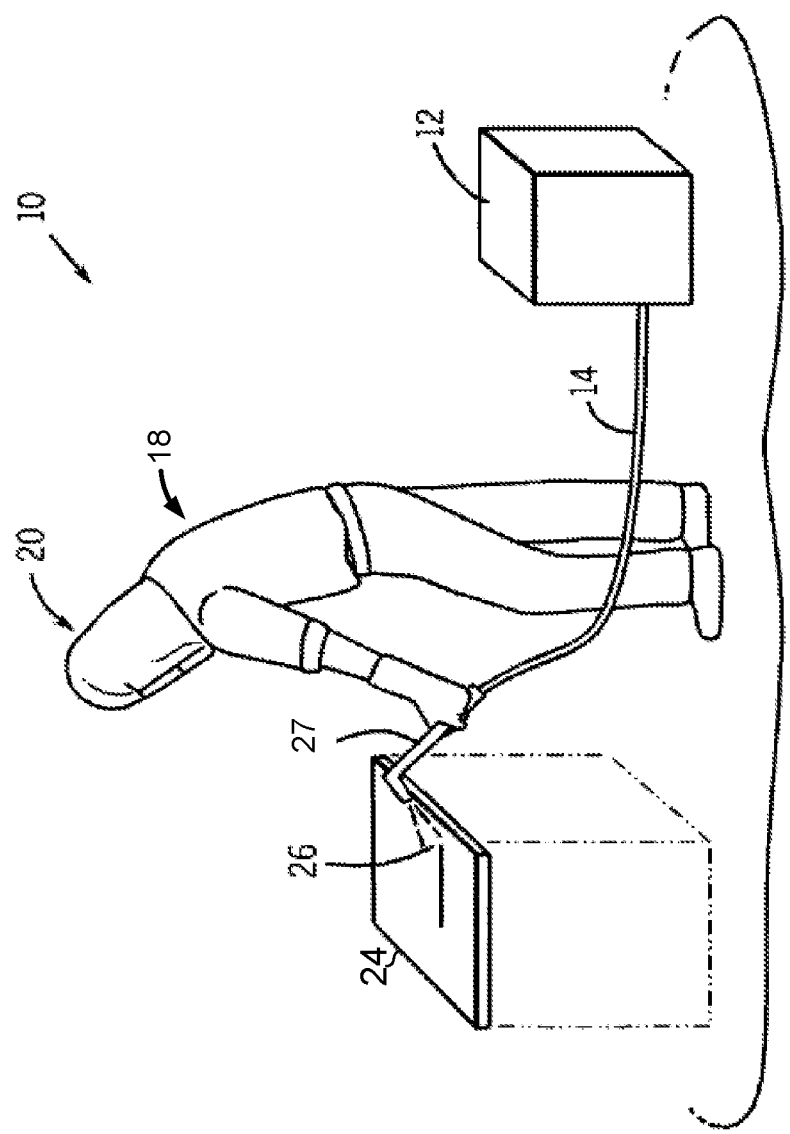
FIG. 1 shows an exemplary arc welding system in accordance with aspects of this disclosure.

As utilized herein the terms "circuits" and "circuitry" refer to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. In other words, "x and/or y" means "one or both of x and y". As another example, "x, y, and/or z" means any element of the seven-element set {(x), (y), (z), (x, y), (x, z), (y, z), (x, y, z)}. In other words, "x, y and/or z" means "one or more of x, y and z". As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled or not enabled (e.g., by a user-configurable setting, factory trim, etc.).

Disclosed example head-worn devices include a camera to generate first pixel data from a field of view of the head-worn device; a display device to display second pixel data to a wearer of the head-worn device based on the first pixel data captured by the camera; weld detection circuitry to: determine whether a welding arc is present; and generate a control signal indicating a result of the determination; and pixel data processing circuitry to process the first pixel data captured by the camera to generate the second pixel data for display on the display device, wherein a mode of operation of said pixel data processing circuitry is selected from a plurality of modes based on said control signal.

Some example head-worn devices further include a receiver circuit to receive a communication, in which the weld detection circuitry determines whether the welding arc is present based on the communication. In some examples, the weld detection circuitry detects an electromagnetic field associated with the welding arc and determines whether the welding arc is present based on the electromagnetic field.

In some examples, the weld detection circuitry receives a signal representative of a weld current flowing through a weld torch and determines whether the welding arc is present based on the signal. In some such examples, the mode of operation of the pixel data processing circuitry is selected based on a weld current level indicated by the signal. In some such examples, the signal includes a communication from at least one of a welding-type power supply, a wire feeder, or a welding-type torch.

Some example head-worn devices further include a microphone to receive an audio signal, in which at least one of processing the first pixel data or the mode of operation of the pixel data processing circuitry is based on the audio signal. In some examples, the weld detection circuitry determines whether the welding arc is present based on receiving a signal indicative of whether the welding arc is present. In some examples, the weld detection circuitry receives one or more signals from a corresponding one or more of a temperature sensor, an accelerometer, a touch sensor, or a gesture sensor, and determines whether the welding arc is present based on the one or more signals. In some examples, the display device overlays the second pixel data over a real view to create an augmented reality view for the wearer of the display device.

Disclosed example head-worn devices include: a display device to display pixel data to a wearer of the head-worn device; weld detection circuitry to determine whether a welding arc is present and generate a control signal indicating a result of the determination; and pixel data processing circuitry to generate the pixel data for display on the display device based on the control signal to provide an augmented reality display.

In some examples, a mode of operation of the pixel data processing circuitry is selected from a plurality of modes based on said control signal. In some examples, one or more objects from a set of predetermined objects are rendered for output on the display device by the pixel data processing circuitry based on said control signal. In some examples, the display device displays the pixel data such that pixels defined in the pixel data are overlaid onto a real view through the display device. In some such examples, the display device displays the pixel data such that at least a portion of the display device is transparent, in which the portion of the display device corresponds to undefined pixels in the pixel data or pixels defined in the pixel data as transparent.

Some example head-worn devices further include a receiver circuit to receive a communication, in which the weld detection circuitry determines whether the welding arc is present based on the communication. In some examples, the weld detection circuitry detects an electromagnetic field associated with the welding arc and determines whether the welding arc is present based on the electromagnetic field.

In some examples, the weld detection circuitry receives a signal representative of a weld current flowing through a weld torch and determines whether the welding arc is present based on the signal. Some example head-worn devices further include a microphone to receive an audio signal, in which at least one of the processing the pixel data or a mode of operation of the pixel data processing circuitry is based on the audio signal. In some examples, the weld detection circuitry receives one or more signals from a corresponding one or more of a temperature sensor, an accelerometer, a touch sensor, or a gesture sensor, and determines whether the welding arc is present based on the one or more signals.

Referring to FIG. 1, there is shown an example welding system 10 in which an operator 18 is wearing welding headwear 20 and welding a workpiece 24 using a torch 27 to which power or fuel is delivered by equipment 12 via a conduit 14. The equipment 12 may comprise a power or fuel source, optionally a source of an inert shield gas and, where wire/filler material is to be provided automatically, a wire feeder. The welding system 10 of FIG. 1 may be configured to form a weld joint by any known technique, including flame welding techniques such as oxy-fuel welding and electric welding techniques such as shielded metal arc welding (i.e., stick welding), metal inert gas welding (MIG), tungsten inert gas welding (TIG), and resistance welding.

Optionally in any embodiment, the welding equipment 12 may be arc welding equipment that provides a direct current (DC) or alternating current (AC) to a consumable or non-consumable electrode of a torch 27. The electrode delivers the current to the point of welding on the workpiece 24. In the welding system 10, the operator 18 controls the location and operation of the electrode by manipulating the torch 27 and triggering the starting and stopping of the current flow. When current is flowing, an arc 26 is developed between the electrode and the workpiece 24. The conduit 14 and the electrode thus deliver current and voltage sufficient to create the electric arc 26 between the electrode and the workpiece. The arc 26 locally melts the workpiece 24 and welding wire or rod supplied to the weld joint (the electrode in the case of a consumable electrode or a separate wire or rod in the case of a non-consumable electrode) at the point of welding between electrode and the workpiece 24, thereby forming a weld joint when the metal cools.

Figure 2:
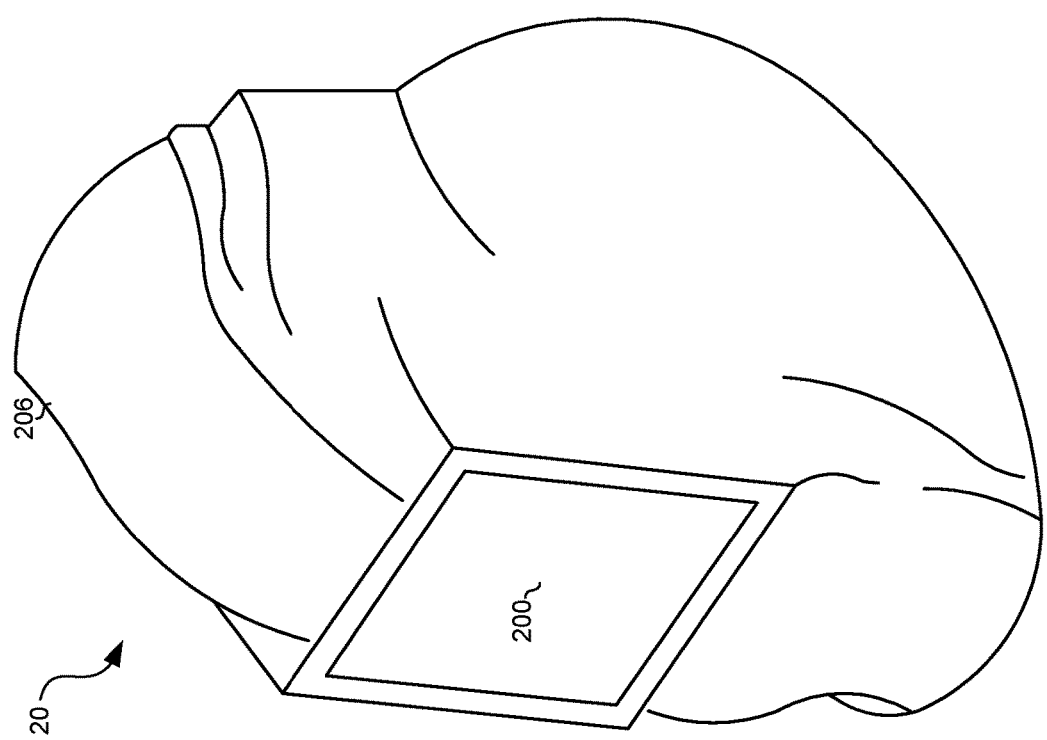
FIG. 2 shows example welding headwear in accordance with aspects of this disclosure.
Figure 3A:
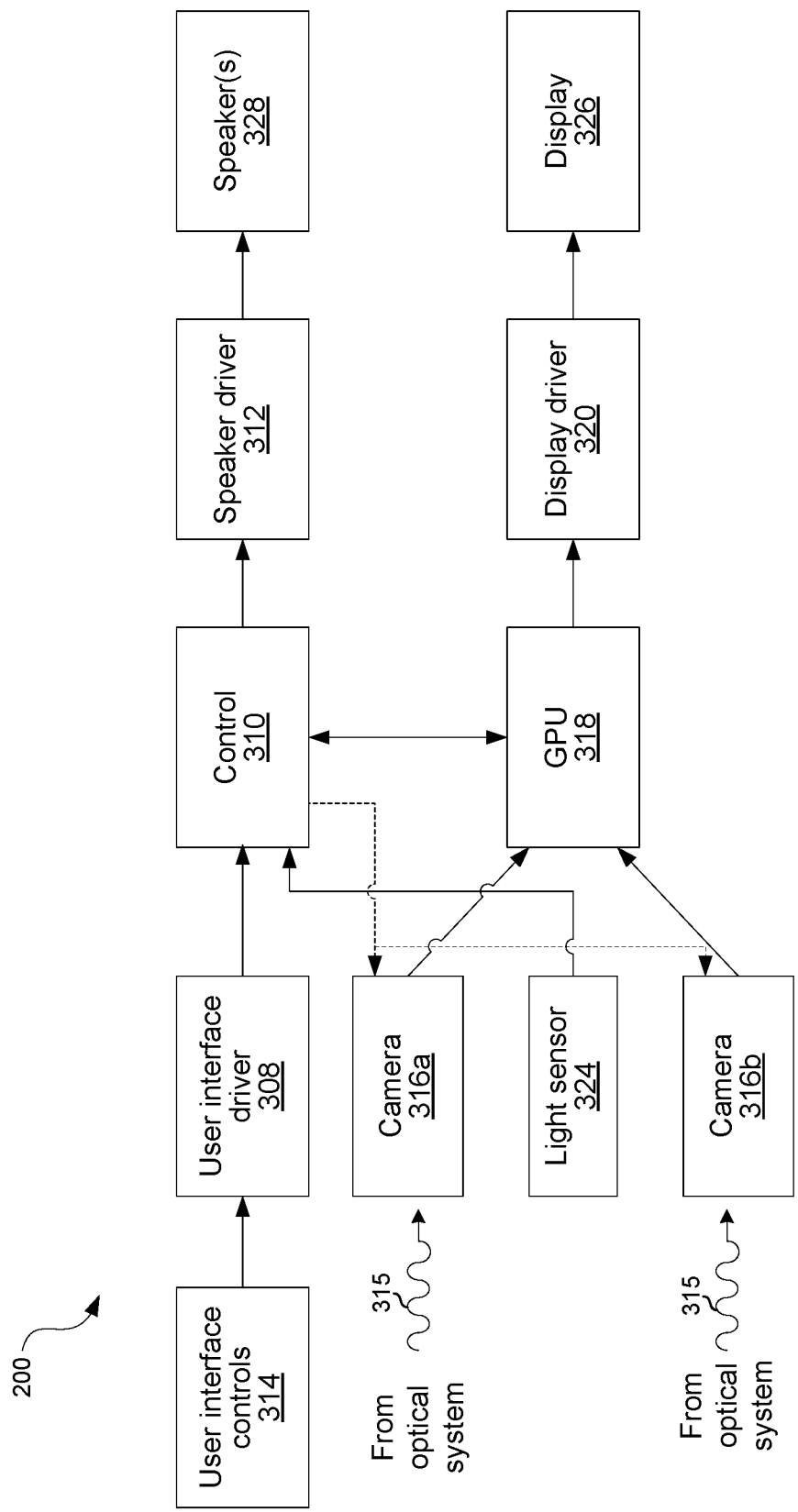
FIG. 3A shows example circuitry of the welding headwear of FIG. 2.
Figure 3B:
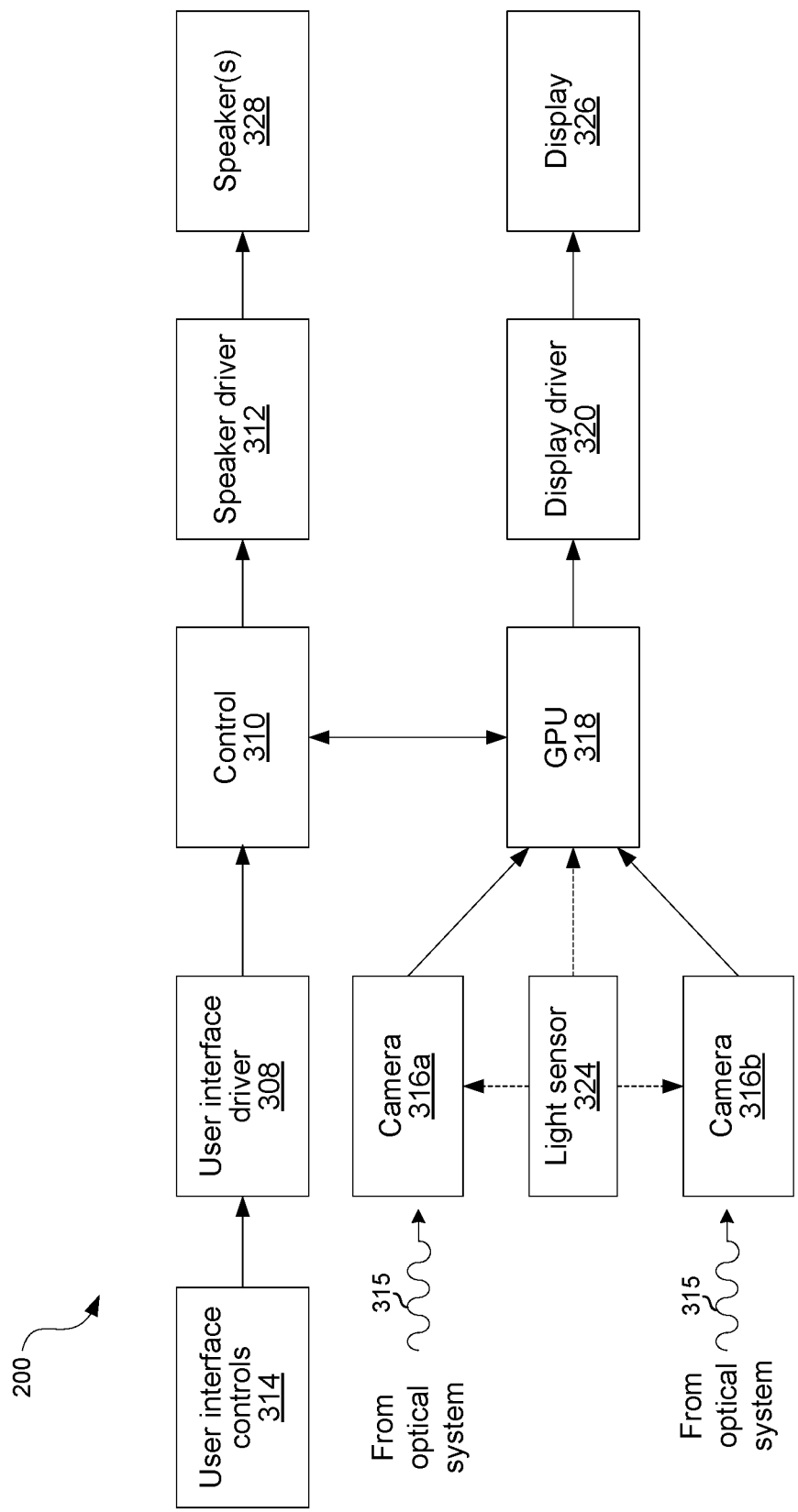
FIG. 3B shows example circuitry of the welding headwear of FIG. 2.
Figure 3C:
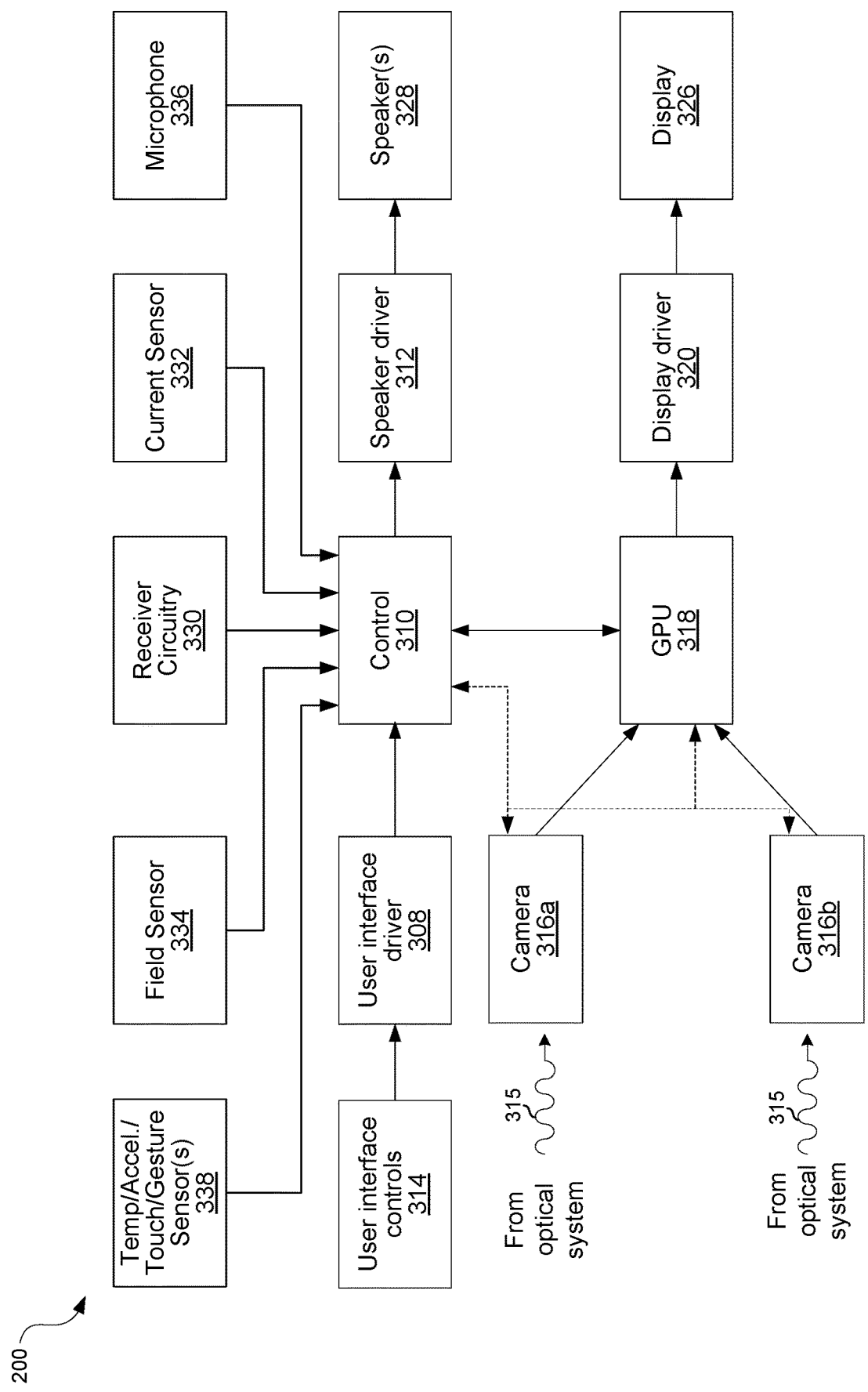
FIG. 3C shows example circuitry of the welding headwear of FIG. 2.

FIG. 2 shows example welding headwear in accordance with aspects of this disclosure. The example headwear 20 is a helmet comprising a shell 206 in or to which is mounted circuitry 200, example details of which are shown in FIGS. 3A-3C. In other implementations, some or all of the circuitry 200 may not be in headwear but may be in, for example, a welding torch, welding power supply, welding apron, welding gloves, and/or any other welding related accessory.

In FIGS. 3A-3C the circuitry 200 comprises user interface controls 314, user interface driver circuitry 308, a control circuit 310, speaker driver circuitry 312, speaker(s) 328, cameras 316a and 316b, graphics processing unit (GPU) 318, display driver circuitry 320, and display 326. In other embodiments, rather than a helmet, the headwear may be, for example, a mask, glasses, goggles, an attachment for a mask, an attachment for glasses, an attachment for goggles, or the like.

The user interface controls 314 may comprise, for example, one or more touchscreen elements, microphones, physical buttons, and/or the like that are operable to generate electric signals in response to user input. For example, user interface controls 314 may comprise capacitive, inductive, or resistive touchscreen sensors mounted on the back of the display 326 (i.e., on the outside of the helmet 20) that enable a wearer of the helmet 20 to interact with user graphics displayed on the front of the display 326 (i.e., on the inside of the helmet 20).

The user interface driver circuitry 308 is operable to condition (e.g., amplify, digitize, etc.) signals from the user interface component(s) 314 for conveying them to the control circuit 310.

The control circuitry 310 is operable to process signals from the user interface driver 308, the GPU 318, and the light sensor 324 (FIG. 3A) or one or both of the cameras 316a and 316b (FIG. 3C). Signals from the user interface driver 308 may, for example, provide commands for setting various user preferences such as display settings (e.g., brightness, contrast, saturation, sharpness, gamma, etc.) and audio output settings (e.g., language, volume, etc.). Signals from the GPU 318 may comprise, for example, information extracted from pixel data processed by the CPU, current settings/state/etc. of the GPU 318, and/or the like. Signals from the cameras 316a and 316b (FIG. 3C) may comprise, for example, information extracted from pixel data captured by the cameras, current settings/state/etc. of the cameras 316, and/or the like.

The control circuit 310 is also operable to generate data and/or control signals for output to the speaker driver 312, the GPU 318, and the cameras 316a and 316b (FIGS. 3A and 3C). Signals to the speaker driver 312 may comprise, for example, audio data for output via the speakers 328, control signals to adjust settings (e.g., volume) of the output audio, and/or the like. Signals to the GPU 318 may comprise, for example, control signals to select and/or configure pixel data processing algorithms to perform on the pixel data from the cameras 316a and 316b. Signals to the cameras 316 may comprise, for example, control signals to select and/or configure shutter speed, f-number, white balance, and/or other settings of the cameras 316.

The speaker driver circuitry 312 is operable to condition (e.g., convert to analog, amplify, etc.) signals from the control circuitry 310 for output to one or more speakers of the user interface components 208.

The cameras 316a and 316b are operable to capture electromagnetic waves of, for example, infrared, optical, and/or ultraviolet wavelengths. Each of cameras 316a and 316b may, for example, comprise an optical subsystem and two sets of one or more image sensors (e.g., two sets of one image sensor for monochrome or two sets of three image sensors for RGB). The two sets of optics may be arranged to capture stereoscopic pixel data such that the resulting images presented on display 326 appear to the wearer of headwear 20 as if seen directly by his/her eyes.

FIG. 3C illustrates additional sources of data that are usable by the control circuit 310 to determine whether a welding arc is present. In the example of FIG. 3C, the circuitry 200 may include one or more of receiver circuitry 300, a current sensor 332, a field sensor 334, a microphone 336, and/or one or more sensor(s) 338, such as a temperature sensor, an accelerometer, a touch sensor, and/or a gesture sensor. As an alternative to detecting a welding arc via the cameras 316*a* or 316*b* and/or via the light sensor 324 (FIG. 3*b*), the example control circuit 310 receives one or more signals from the receiver circuitry 330, a current sensor 332, a field sensor 334, a microphone 336, and/or one or more sensor(s) 338 and determines whether the welding arc is present based on the received signals.

The receiver circuitry 330 receives a communication or other signal that indicates whether a weld current is flowing through the weld torch. A signal or communication may be received from, for example, an external current sensor, a weld torch trigger, a wire feeder, and/or any other device capable of detecting or measuring current in the weld circuit. When a signal or communication is received at the receiver circuitry 330, the control circuit 310 determines whether the welding arc is present based on the communication.

The current sensor 332 may provide a signal to the control circuit 310 that is representative of a weld current flowing through a weld torch. Based on the signal, the control circuit 310 determines whether the welding arc is present based on the signal. In some examples, the mode of operation of the pixel data processing circuitry is selected based on the weld current level indicated by the signal output from the current sensor 332. The signal may include a communication from at least one of a welding-type power supply, a wire feeder, or a welding-type torch. The mode of operation may be selected based on a weld current level indicated by the signal.

The field sensor 334 detects an electromagnetic field associated with the welding arc. For example, the field sensor 334 may be coupled to an antenna to identify one or more frequencies of interest that correspond to a welding arc. The control circuit 310 may determine whether the welding arc is present based on the electromagnetic field and/or the frequency components of the electromagnetic field detected by the field sensor 334.

The microphone 336 receives audio signal(s). Welding is associated with identifiable sounds. The control circuit 310 and/or the GPU 318 may process the pixel data and/or select a mode of operation based on processing the audio signal.

The control circuit 310 may receive one or more signals from the one or more sensors 338. For example, the control circuit 310 may receive signals from the temperature sensor (e.g., infrared temperature near the workpiece), an accelerometer (e.g., torch orientation and/or torch movement information), a touch sensor (e.g., holding a welding torch and/or touching the torch trigger), and/or a gesture sensor (e.g., recognizing a gesture associated with an operator welding). The control circuit 310 determines whether the welding arc is present based on the one or more signals from the one or more sensors.

Figure 4:
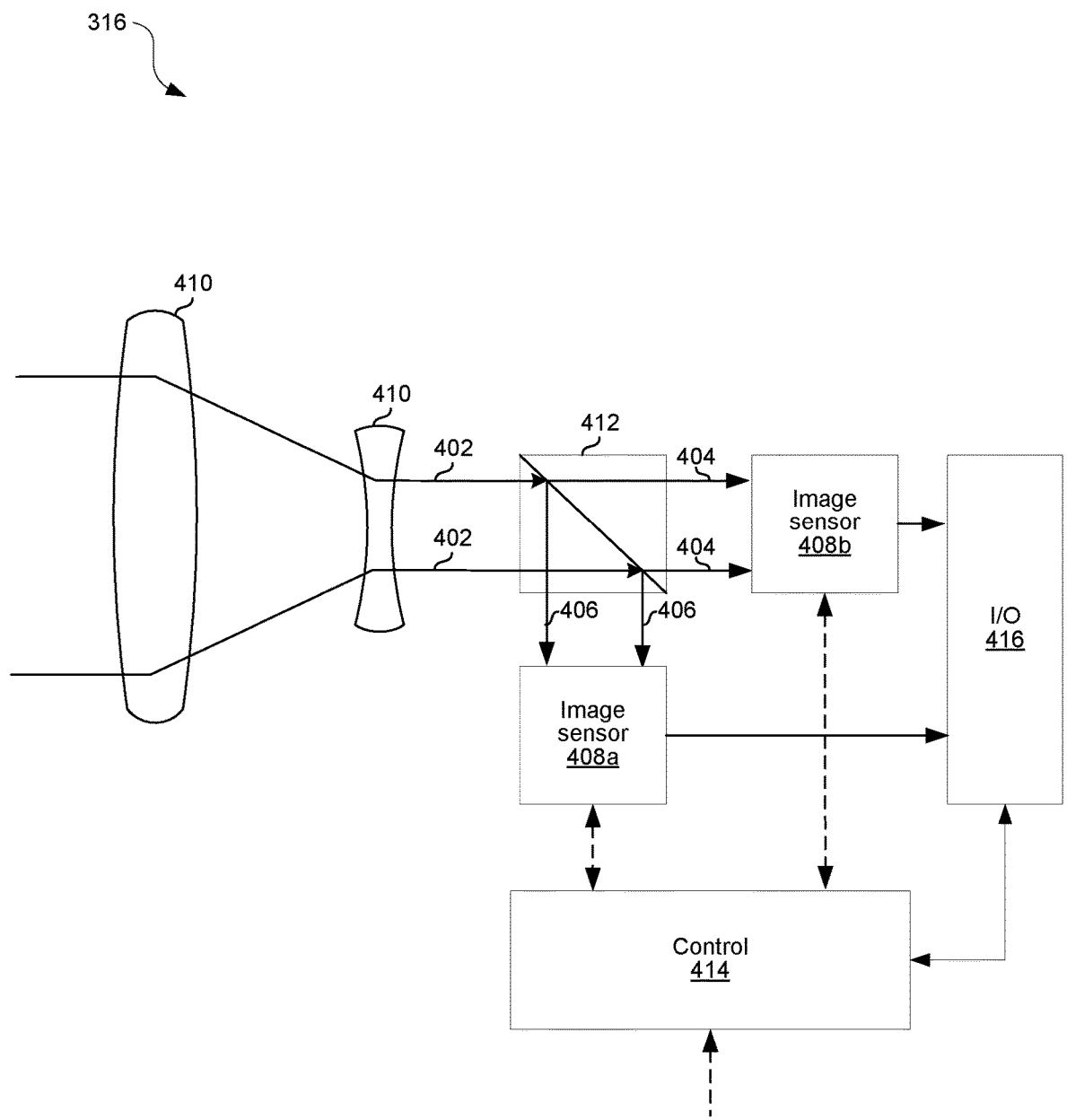
FIG. 4 shows example optical components of the welding headwear of FIG. 2.

Referring briefly to FIG. 4, an example implementation of a camera 316 is shown. The example implementation of the camera 316 shown in FIG. 4 comprises lenses 410, beam splitter 412, image sensors 408*a* and 408*b*, control circuitry 414, and input/output circuitry 416. The image sensors 408*a* and 408*b* comprise, for example, CMOS or CCD image sensors operable to convert optical signals to digital pixel data and output the pixel data to input/output circuit 416. The input/output circuit 416 may output the pixel data in serial or parallel in accordance with protocols agreed on between the camera 316 and the GPU 318. The control circuitry 414 is operable to generate signals for configuring/controlling operation of the image sensors 408*a* and 408*b* and I/O circuit 416. The control circuit 414 may be operable to generate such control signals based on other control signals received from, for example, light sensor 324 and/or control circuit 310.

In operation, light beams 402 are focused onto beam splitter 412 by lenses 410. A first portion of beams 402 are reflected by the splitter 412 to arrive at image sensor 408*a* as beams 406. A second portion of beams 402 pass through the splitter 412 to arrive at image sensor 408*b* as beams 404. The image sensors 408*a* and 408*b* concurrently capture (i.e., their respective shutters are open for overlapping time periods) respective frames of the same image, but with different settings (e.g., different shutter speeds). The pixel data streams are then output to I/O circuit 416 which, in turn, relays them to GPU 318. The GPU 318 may then combine the two pixel streams to, for example, achieve an image with contrast that is better than can be achieved by either of the image sensors 408*a* and 408 individually. The example shown is a monochrome implementation since there is only one image sensor for beams 404 and one image sensor for beams 406. In an example color implementation, beams 404 may be further split and pass through color-selective filters in route to a plurality of image sensors 408*b* and beams 406 may be further split and pass through color-selective filters in route to a plurality of image sensors 408*a*.

In another example implementation, sufficient contrast may be achieved with only a single image sensor 408 (or set of image sensors 408 for color) per camera 316. This may be achieved, for example, with a high dynamic range image sensor or simply result from the fact that relatively lower dynamic range is sufficient in some applications (e.g., in an augmented reality application where the pixel data is overlaid on the real view instead of a mediated reality in which everything the viewer sees is a processed image).

Likewise, in some example implementations, stereo vision may not be needed and thus only a single camera 316 may be used.

Returning to FIGS. 3A-3C, the light sensor 324 (FIGS. 3A and 3B) comprises circuitry operable to measure the intensity of light incident on the headwear 20. The light sensor 324 may comprise, for example, a photodiode or passive infrared (IR) sensor, along with associated drive electronics (e.g., amplifiers, buffers, logic circuits, etc.). The measured intensity (e.g., measured in candelas) may be used to determine when a welding arc is struck. In an example implementation, there may be multiple light sensors 324 which sense light intensity from multiple directions. For example, a first sensor 324 may sense the intensity of light incident on the front of the headwear 20 (light which may be directly incident on the headwear 20 from a welding arc) and a second sensor may sense the intensity of light incident on the back of the headwear 20 (which may be shielded from direct light from the welding arc). The different readings from various light sensors 324 may be used to determine information about the lighting environment, which may, in turn, be used for controlling the pixel data processing algorithms used for processing pixel data from the cameras 316*a* and 316*b* for presentation on the display 326.

The graphics processing unit (GPU) 318 is operable to receive and process input pixel data from the cameras 316a and 316b. The processing of pixel data by the GPU 318 may extract information from the pixel data and convey that information to control circuit 310. The processing of pixel data by the GPU 318 may result in the generation of output pixel data for conveyance to the display driver 320. In an example implementation, the pixel data output from the GPU 318 to the display driver 320 (and ultimately to display 326) may provide a mediated-reality view for the wearer of the headwear 20. In such a view, the wearer experiences the video presented on the display 326 as if s/he is looking through a lens, but with the image enhanced and/or supplemented by an on-screen display. The enhancements (e.g., adjust contrast, brightness, saturation, sharpness, gamma, etc.) may enable the wearer of the helmet 20 to see things s/he could not see with simply a lens (e.g., through contrast control). The on-screen display may comprise text, graphics, etc. overlaid on the video to, for example, provide visualizations of equipment settings received from the control circuit 310 and/or visualizations of information determined from the analysis of the pixel data. In another example implementation, the pixel data output from the GPU 318 may be overlaid on a real view seen through a transparent or semi-transparent lens (such as an auto-darkening lens found on conventional welding headwear). Such overlaid information may comprise text, graphics, etc. overlaid on the video to, for example, provide visualizations of equipment settings received from the control circuit 310 and/or visualizations of information determined from the analysis of the pixel data.

In an example implementation, the processing of pixel data by the GPU 318 may comprise the implementation of pixel data processing algorithms that, for example, determine the manner in which multiple input streams of pixel data from multiple cameras 316 are combined to form a single output stream of pixel data. Configuration of pixel data processing algorithms performed by GPU 318 may comprise, for example, configuration of parameters that determine: characteristics (e.g., brightness, color, contrast, sharpness, gamma, etc.) of the streams prior to combining; characteristics (e.g., brightness, color, contrast, sharpness, gamma, etc.) of the combined stream; and/or weights to be applied to pixel data from each of the multiple streams during weighted combining of the multiple streams. In an example implementation using weighted combining of input pixel streams, the weights may be applied, for example, on a pixel-by-pixel basis, set-of-pixels-by-set-of-pixels basis, frame-by-frame basis, set-of-frames-by-set-of-frames basis, or some combination thereof. As one example, consider weighted combining of three frames of two input pixel streams where weights of 0, 1 are used for the first frame, weights 0.5, 0.5 are used for the second frame, and weights 1, 0 are used for the third frame. In this example, the first frame of the combined stream is the first frame of the second input stream, the second frame of the combined stream is the average of the second frames of the two input streams, and the third frame of the combined stream is the third frame of the first input stream. As another example, consider weighted combining of three pixels of two input pixel streams where weights of 0, 1 are used for the first pixel, weights 0.5, 0.5 are used for the second pixel, and weights 1, 0 are used for the third pixel. In this example, the first pixel of the combined stream is the first pixel of the second input stream, the second pixel of the combined stream is the average of the second pixels of the two input streams, and the third pixel of the combined stream is the third pixel of the first input stream.

As mentioned above, in other implementations, stereovision may not be needed and thus a single camera 316 may be sufficient. Also, in some implementations, sufficient contrast may be achieved with a single (or single set) of image sensors and there may be no need for the combining of bright and dark pixel streams to enhance contrast. As an example, where it is desired to capture pixel data only when the welding arc is present (as indicated by the light sensor 324), then the system may use only a single camera 316 with single image sensor (or set of image sensors for color) configured for capturing pixel data in the presence of the arc.

In other example implementations, no cameras 316 at all may be present. This may include, for example, an augmented reality application in which pixel data comprising only predetermined objects (e.g., graphics, text, images captured by means other than the headwear 20, etc.) is rendered for output onto the display 306. Which objects are rendered, and/or characteristics (e.g., color, location, etc.) of those objects, may change based on whether the light sensor indicates the arc is present or not. In some examples, the display 306 overlays pixel data of rendered objects over a real view to create an augmented reality view for the wearer of the display 306.

The display driver circuitry 320 is operable to generate control signals (e.g., bias and timing signals) for the display 326 and to process (e.g., level control synchronize, packetize, format, etc.) pixel data from the GPU 318 for conveyance to the display 326.

The display 326 may comprise, for example, two (in implementations using stereoscopic viewing) LCD, LED, OLED, E-ink, and/or any other suitable type of panels operable to convert electrical pixel data signals into optical signals viewable by a wearer of the helmet 20.

In operation, a determination of the intensity of light incident on the cameras 316a and 316b during capture of a pair of frames may be used for configuring the pixel data processing algorithm that performs combining of the two frames and/or may be used for configuring settings of the camera 316a and 316b for capture of the next pair of frames.

In the example implementations of FIGS. 3A and 3B, the light intensity is measured by one or more light sensors 324. Each light sensor may comprise, for example a photodiode or passive IR sensor that is sensitive to wavelengths in the visible spectrum. The measurement from the light sensor(s) 324 may then be used to configure pixel data capture settings (e.g., shutter speeds, f-numbers, white balance, etc.) of the cameras 316a and 316b. Additionally, or alternatively, the measurement from the light sensor(s) 324 may be used to select and/or configure pixel data processing algorithms performed on the captured pixel data by the GPU 318. In the example implementation of FIG. 3A, the measurement may be conveyed to the control circuit 310 which may then perform the configuration of the cameras 316a and 316b and/or the GPU 318. In the example implementation of FIG. 3B, the measurement from the light sensor(s) 324 may be conveyed directly to the cameras 316a and 316b and/or GPU 318, which may then use the measurement to configure themselves.

In the example implementation of FIG. 3C, rather than using a light sensor 324 that is distinct from the image sensors 408a and 408b, a measurement of light intensity is generated based on the pixel data captured by the cameras 316a and 316b. For example, each camera may calculate average luminance over groups of pixels of a frame and/or groups of frames. The calculated luminance value(s) may then be conveyed to the control circuit 310 and/or GPU 318 which may then configure the settings of the cameras 316a and 316b and/or configure the pixel data processing algorithms used to combine the pixel data from the two image sensors. The cameras 316a and 316b may also use the calculated luminance value(s) in a feedback loop for configuring their settings (such as timing and/or speed of an electronic and/or mechanical shutter, and/or some other electric, mechanical, or electromechanical operation or system in the cameras 316a and 316b).

Figure 5:
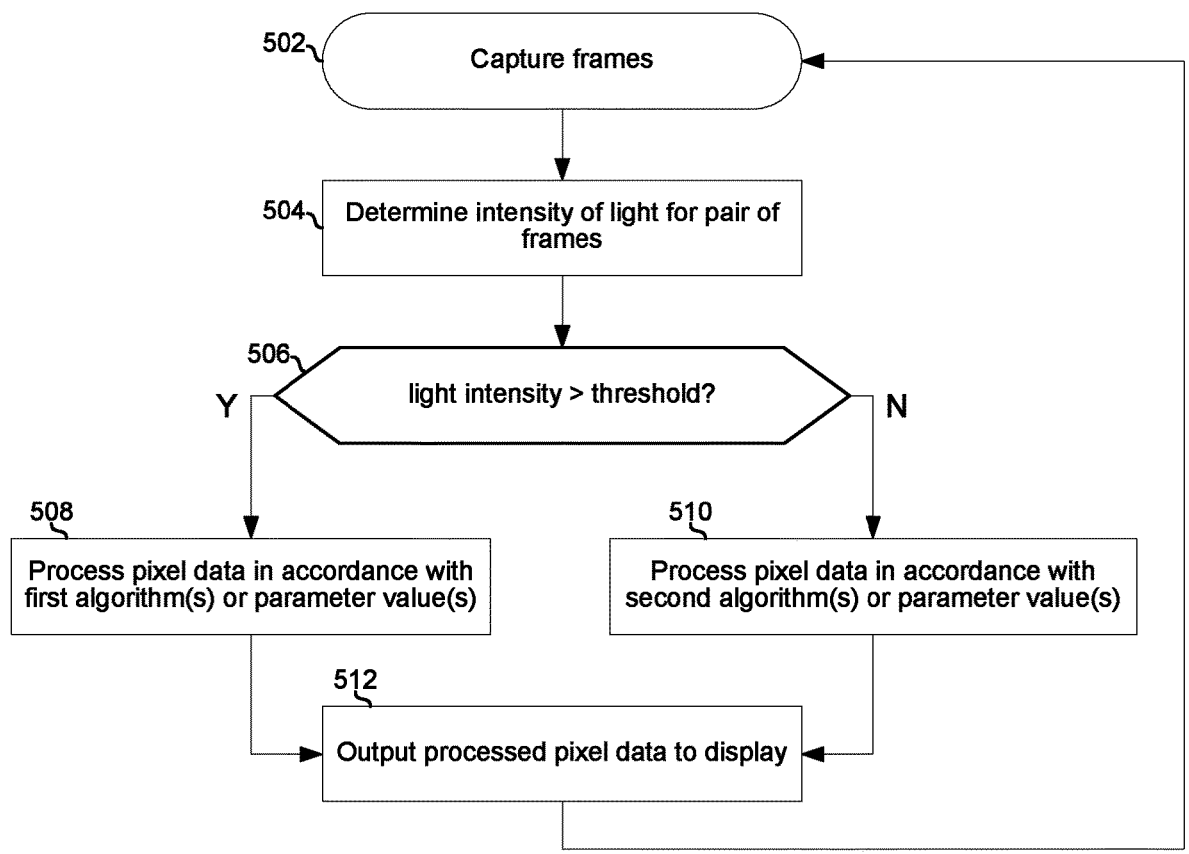
FIG. 5 is a flowchart illustrating an example process for controlling pixel data processing in the headwear of FIG. 2.

Operation of the various implementations shown in FIGS. 3A-3D is now described with reference to FIG. 5.

In block 502, two frames are captured by the cameras 316a and 316b. The cameras 316a and 316b are synchronized such that the two frames are captured simultaneously (within an acceptable timing tolerance). The two frames are captured with different settings such that they provide diversity of captured information. For example, image sensor 416a may use a slower shutter speed and/or lower f-number (and be referred to herein as the "bright image sensor") and the image sensor 416b may use a faster shutter speed and/or higher f-number (and be referred to herein as the "dark image sensor"). As an example, for frames captured while a welding arc is very bright, the bright image sensor may be overexposed while the dark image sensor provides an image that provides sufficient contrast for the wearer of the headwear 20 to clearly see the weld pool, arc, weld metal, workspace, and weld joint surroundings such that s/he can lay down a high-quality weld. Continuing this example, for frames captured while a welding arc is not present, the dark image sensor may be underexposed while the bright image sensor provides an image that provides sufficient contrast for the wearer of the headwear 20 to clearly see the weld pool, arc, weld metal, workspace, and weld joint surroundings such that s/he can lay down a high-quality weld.

In block 504, the light intensity incident on the cameras 316a and 316b during capture of a pair of frames is determined through direct measurement or indirect measurement. Direct measurement may comprise, for example, measurement by one or more light sensors 324 (FIGS. 3A and 3B) and/or the image sensors 408a and 408b. An example of indirect measurement is use of an arc monitoring tool to measure amperage delivered from the torch 204 to the workpiece 24 and then calculating lux based on the measured amperage, the type of torch, type of workpiece (e.g., type of metal), etc.

In block 506, the intensity of light measured in block 504 is compared to a determined threshold. The threshold may be fixed or may be dynamic. An example where the threshold is dynamic is where the threshold is adapted through one or more feedback loops (e.g., based on light intensity measured during previously-captured frames). Another example where the threshold is dynamic is where it is configurable based on input from user interface controls 314 (e.g., a user may adjust the threshold based on his/her preferences). In an example implementation, the threshold is set such that the comparison distinguishes between frames captured while a welding arc was struck and frames capture when no welding arc was present. If the light intensity measured in block 504 is above the threshold, then the process advances to block 508.

In block 508, the GPU 318 processes the frames of pixel data from cameras 316a and 316b using a first one or more algorithms and/or a first one or more parameters values. The one or more algorithms may be selected from a larger set of algorithms available to the GPU 318 and/or the first one or more parameter values may be selected from a larger set of possible values. In this manner, the algorithms, and/or parameter values used thereby, are determined based on the result of the comparison of block 506.

In block 512, the process pixel data is output from GPU 318 to display driver 320.

Returning to block 506, if the intensity of light measured in block 504 is not above the threshold, then the process advances to block 510.

In block 510, the GPU 318 processes the frames of pixel data from cameras 316a and 316b using a second one or more algorithms and/or a second one or more parameter values. The one or more algorithms may be selected from a larger set of algorithms available to the GPU 318 and/or the first one or more parameter values may be selected from a larger set of possible values. In this manner, the algorithms, and/or parameter values used thereby, are determined based on the result of the comparison of block 506.

In an example implementation, block 508 corresponds to simply selecting one of the two frames from cameras 316a and 316b and discarding the other of the two frames, and block 510 corresponds to combining the two frames to form a new combined frame (e.g., where the combined frame has higher contrast than either of the two original frames).

In an example implementation, block 508 corresponds to applying a first set of pixel post-processing parameter values (e.g., for adjusting brightness, color, contrast, saturation, gamma, etc.) to the two frames during combining of the two frames, and the block 510 corresponds to applying a second set of pixel post-processing parameter values to the two frames during combining of the two frames.

Figure 6B:
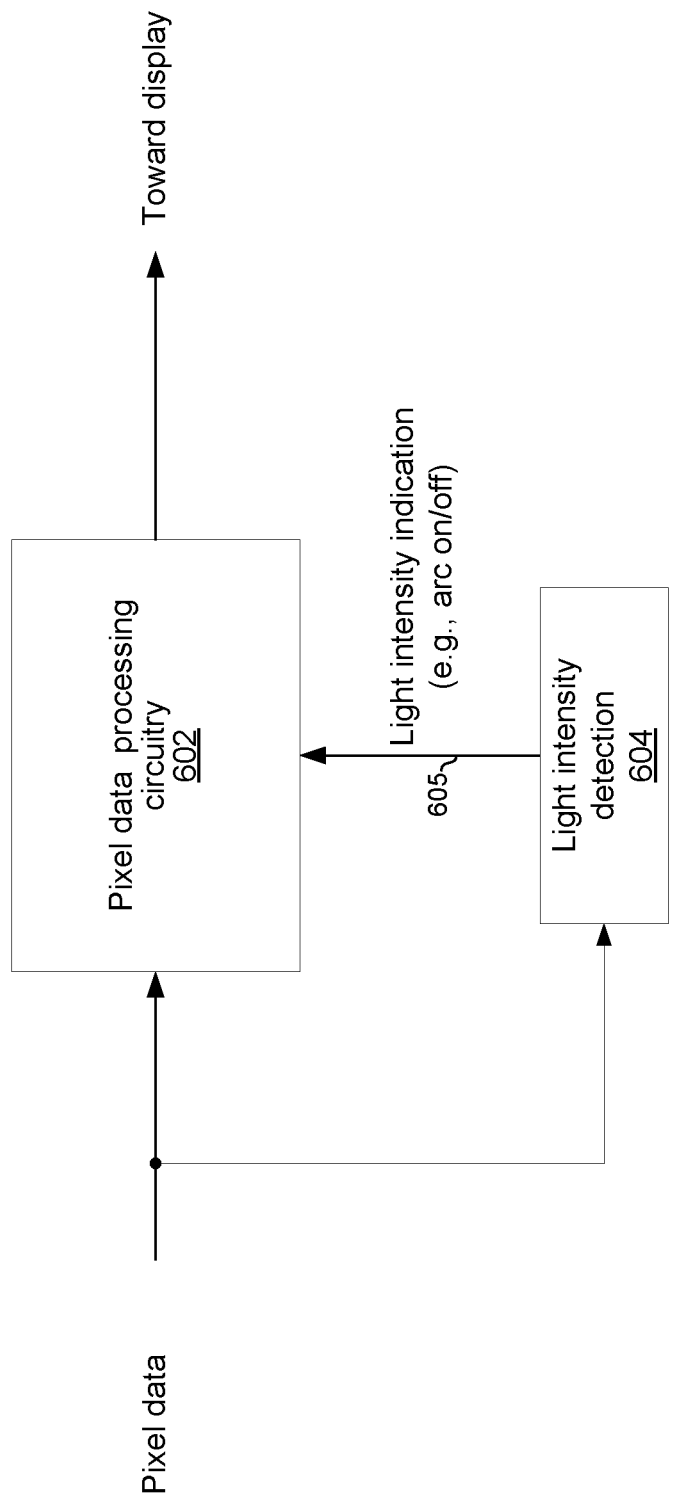

FIGS. 6A and 6B are block diagrams of example circuitry for controlling pixel processing based on a detection of light intensity. Shown in FIGS. 6A and 6B are pixel data processing circuitry 602 and light intensity detection circuitry 604. The pixel data processing circuitry 602 may comprise, for example, circuitry the GPU 318, circuitry of the camera(s) 316, display driver circuitry 320, and/or circuitry of the display 326. The light intensity detection circuitry 604 may comprise, for example, the light sensor 324, circuitry of the GPU 318, and/or circuitry of the camera(s) 316. In the implementation of FIG. 6B, the light intensity detection circuitry 604 also processes pixel data and may be considered pixel data processing circuitry in such an implementation.

In FIG. 6A, the light intensity detection circuitry 604 directly captures light incident on it and sets the value of control signal 605 based on the intensity of the light according to some function, logic operation, etc. For example, in FIG. 6A the light intensity detection circuitry 604 may comprise a photodiode or passive IR sensor that is mounted on the outside of the headwear 20 facing the likely direction of the welding arc. The light detection circuitry 604 may, for example, convert (e.g., through any suitable circuitry such as an ADC, a comparator, etc.) the light incident on it to a 1-bit signal 605 that indicates arc weld present or absent. As another example, the signal 605 may be an analog signal or multi-bit digital signal capable of representing additional decision levels (e.g., 2 bits for arc definitely absent, arc probably absent, arc probably present, and arc definitely present; myriad other possibilities of course exist). The pixel data processing circuitry 602 receives the signal 605 and configures the operations it performs on the pixel data in response to the state of signal 605. For example, when signal 605 is low, indicating the arc is absent, the pixel data processing circuitry may process the pixel stream in a first manner (e.g., using a first set of weighting coefficients for combining two pixel streams) and when signal 605 is high, indicating the arc is present, the pixel data processing circuitry may process the pixel stream in a second manner (e.g., using a second set of weighting coefficients for combining two pixel streams).

FIG. 6B is similar to FIG. 6A but with the light intensity detection circuitry 604 determining intensity from the pixel data itself. For example, the light intensity detection circuitry 604 may compare the pixel values (e.g., on a pixel-by-pixel basis, pixel-group-by-pixel-group basis, or the like) to determine whether the arc was present during the capture of the pixel(s) currently being processed.

In an implementation such as FIG. 6B, the light detection circuitry 604 may be fast enough such that it is able to make its decision and configure the signal 605 without requiring the pixel data to be buffered longer than would introduce a noticeable lag. In this regard, in some instances the circuitry 604 may be capable of generating a decision and configuring signal 605 within a single pixel clock cycle, thus avoiding need for any additional buffering of the pixel data stream.

In accordance with an example implementation of this disclosure, a system (e.g., a welding system comprising one or both of headwear 20 and equipment 12) comprises light intensity detection circuitry (e.g., 604) and multi-mode circuitry (e.g., any one or more of 308, 312, 314, 316, 318, 320, 324, and may support multiple modes of operation). The light intensity detection circuitry is operable to determine whether a welding arc is present based on an intensity of light incident captured by the light intensity detection circuitry, and generate a control signal (e.g., 605) indicating a result of the determination. A mode of operation of the multi-mode circuitry may be selected from a plurality of modes based on the control signal. The light intensity detection circuitry may comprise, for example, a passive infrared sensor, a photodiode, and/or circuitry of a camera. The multi-mode circuitry may comprise pixel data processing circuitry (circuitry the GPU 318, circuitry of the camera(s) 316, display driver circuitry 320, and/or circuitry of the display 326). The pixel data processing circuitry may comprise, for example, circuitry of a camera, a special purpose graphics processing unit (e.g., 318), and/or a general purpose processing unit. A first of the plurality of modes may use a first exposure value and a second of the plurality of modes use a second exposure value. A first of the plurality of modes may use a first set of weights during weighted combining of pixel data, and a second of the plurality of modes uses a second set of weights during said weighted combining of pixel data. A particular pixel processing operation performed by the pixel data processing circuitry may be disabled when the pixel data processing circuitry is in a first of the plurality of modes, and enabled when the pixel data processing circuitry is in a second of the plurality of modes. Recording of image data by the system may be disabled when the pixel data processing circuitry is in a first of the plurality of modes, and enabled when the pixel data processing circuitry is in a second of the plurality of modes. The light intensity detection circuitry may be operable to update the control signal on a pixel-by-pixel and/or group-of-pixels-by-group-of-pixels basis. Other examples of controlling modes of multi-mode circuitry for providing feedback to the wearer comprise: selecting between on, off, and flashing modes of an LED of the headwear; and selecting between different sounds to be played through a speaker of the headwear.

While the example of the two cameras being configured differently in terms of exposure value is used in this disclosure for purposes of illustration, the configurations of the two image sensors need not differ in, or only in, exposure value. For example, the first camera be configured to have a first shutter timing (that is, when a capture by that camera is triggered) and the second camera may be configured to have a second shutter timing. In such an implementation, for example, the amount of light reaching the camera's image sensors may vary periodically and the two cameras may be synchronized to different phases of the varying light. While this example implementation is used often referred to in this disclosure for purposes of illustration, the two configurations need not differ in, or only in, exposure value. For example, the first configuration may correspond to a first shutter timing (that is, when a capture is triggered) and the second configuration may correspond to a second shutter timing. In such an implementation, for example, the two image sensors may be synchronized with an external light source.

The present method and/or system may be realized in hardware, software, or a combination of hardware and software. The present methods and/or systems may be realized in a centralized fashion in at least one computing system, or in a distributed fashion where different elements are spread across several interconnected computing systems. Any kind of computing system or other apparatus adapted for carrying out the methods described herein is suited. A typical combination of hardware and software may be a general-purpose computing system with a program or other code that, when being loaded and executed, controls the computing system such that it carries out the methods described herein. Another typical implementation may comprise an application specific integrated circuit or chip. Some implementations may comprise a non-transitory machine-readable (e.g., computer readable) medium (e.g., FLASH drive, optical disk, magnetic storage disk, or the like) having stored thereon one or more lines of code executable by a machine, thereby causing the machine to perform processes as described herein.

While the present method and/or system has been described with reference to certain implementations, it will be understood by those skilled in the art that various changes may be made and equivalents may be substituted without departing from the scope of the present method and/or system. In addition, many modifications may be made to adapt a particular situation or material to the teachings of the present disclosure without departing from its scope. Therefore, it is intended that the present method and/or system not be limited to the particular implementations disclosed, but that the present method and/or system will include all implementations falling within the scope of the appended claims.

What is claimed is:

1. A head-worn device, comprising:
   a camera configured to generate first pixel data from a field of view of the head-worn device;
   a display device to display second pixel data to a wearer of the head-worn device based on the first pixel data captured by the camera;
   a field sensor coupled to an antenna and configured to detect an electromagnetic field associated with the welding arc;
   weld detection circuitry configured to:
      determine whether a welding arc is present based on the electromagnetic field; and
      generate a control signal indicating a result of the determination; and
   pixel data processing circuitry configured to process the first pixel data captured by the camera to generate the second pixel data for display on the display device, wherein a mode of operation of said pixel data processing circuitry is selected from a plurality of modes based on said control signal.

2. The head-worn device as defined in claim 1, further comprising a receiver circuit configured to receive a communication, the weld detection circuitry configured to determine whether the welding arc is present based on the communication.

3. The head-worn device as defined in claim 1, wherein the weld detection circuitry is configured to receive a signal representative of a weld current flowing through a weld torch and to determine whether the welding arc is present based on the signal.

4. The head-worn device as defined in claim 3, wherein the mode of operation of the pixel data processing circuitry is selected based on a weld current level indicated by the signal.

5. The head-worn device as defined in claim 3, wherein the signal comprises a communication from at least one of a welding-type power supply, a wire feeder, or a welding-type torch.

6. The head-worn device as defined in claim 1, further comprising a microphone to receive an audio signal, at least one of the processing the first pixel data or the mode of operation of the pixel data processing circuitry being based on the audio signal.

7. The head-worn device as defined in claim 1, wherein the weld detection circuitry is configured to determine whether the welding arc is present based on receiving a signal indicative of whether the welding arc is present.

8. The head-worn device as defined in claim 1, wherein the display device is configured to overlay the second pixel data over a real view to create an augmented reality view for the wearer of the display device.

9. A head-worn device, comprising:
   a camera configured to generate first pixel data from a field of view of the head-worn device;
   a display device to display second pixel data to a wearer of the head-worn device based on the first pixel data captured by the camera;
   weld detection circuitry configured to:
      receive one or more signals from a corresponding one or more of a temperature sensor, an accelerometer, a touch sensor, or a gesture sensor;
      determine whether a welding arc is present based on the one or more signals; and
      generate a control signal indicating a result of the determination; and
   pixel data processing circuitry configured to process the first pixel data captured by the camera to generate the second pixel data for display on the display device, wherein a mode of operation of said pixel data processing circuitry is selected from a plurality of modes based on said control signal.

* * * * *